(12) United States Patent
Tournier et al.

(10) Patent No.: US 6,241,968 B1
(45) Date of Patent: Jun. 5, 2001

(54) COMPOSITIONS FOR INCREASING THE MRI CONTRAST IN VISUALIZING THE DIGESTIVE TRACT OF PATIENTS

(75) Inventors: Hervé Tournier, Valleiry; Philippe Bussat, Feigeres, both of (FR)

(73) Assignee: Bracco Research S.A., Carouge (CH)

( * ) Notice: Subject to any disclaimer, the term of this patent is extended or adjusted under 35 U.S.C. 154(b) by 0 days.

(21) Appl. No.: 09/472,815

(22) Filed: Dec. 28, 1999

Related U.S. Application Data

(62) Division of application No. 08/997,453, filed on Dec. 23, 1997, now Pat. No. 6,060,040.

(30) Foreign Application Priority Data

Dec. 23, 1996 (EP) .................................................. 96810888

(51) Int. Cl.[7] ...................................................... A61B 5/55
(52) U.S. Cl. ................ 424/9.363; 514/184; 514/836; 534/16; 540/465; 540/474
(58) Field of Search ...................... 424/9.363; 600/420; 515/184, 836; 534/16; 540/465, 474; 436/173

(56) References Cited

U.S. PATENT DOCUMENTS

| | | | |
|---|---|---|---|
| 3,331,773 | 7/1967 | Gunderson et al. | 210/58 |
| 5,141,740 | 8/1992 | Rajogopalan et al. | 424/9.364 |
| 5,318,771 | * 6/1994 | Lauffer et al. | 424/9.361 |
| 5,466,439 | 11/1995 | Gibby et al. | 424/9.365 |
| 5,514,379 | 5/1996 | Weissleder et al. | 424/426 |
| 5,514,732 | 5/1996 | Vanderlaan et al. | 523/106 |
| 5,622,688 | * 4/1997 | Uggeri et al. | 424/9.363 |
| 5,676,923 | * 10/1997 | Platzek et al. | 424/9.363 |
| 5,681,544 | 10/1997 | Schmitt-Willich | 424/9.34 |
| 5,746,688 | 5/1998 | Snow et al. | 534/16 |
| 5,746,995 | 5/1998 | Maier et al. | 424/1.65 |
| 5,770,637 | 6/1998 | Vanderlaan et al. | 523/106 |
| 5,801,228 | 9/1998 | Hollister et al. | 534/15 |
| 5,804,164 | 9/1998 | Elgavish | 424/9.364 |
| 5,811,076 | 9/1998 | Brasch et al. | 424/9.363 |

FOREIGN PATENT DOCUMENTS

| | | |
|---|---|---|
| 0 436 316A | 7/1991 | (EP) . |
| 0 635 733 A1 | 1/1995 | (EP) . |
| 1 464 50 | 2/1977 | (GB) . |
| 06016606 | 1/1994 | (JP) . |
| WO 94/00096 | 1/1994 | (WO) . |

* cited by examiner

*Primary Examiner*—Gary E. Hollinden
(74) *Attorney, Agent, or Firm*—Nixon & Vanderhye

(57) ABSTRACT

The invention provides, as contrast signal generators in MR imaging of the digestive tract, paramagnetic metal chelates of novel acrylic compounds of formula $C(R^1R^2)=CR^3-CO-Z-Z$ (1) and/or $C(R^1R^2)=CR^3-CO-Z-Z-Z-CO-CR^3=C(R^1R^2)$ (2) in monomer, oligomer, homopolymer and copolymer forms, in which the $R^1$, $R^2$ and $R^3$ represent H or saturated or unsaturated $C_{1-10}$ aliphatic radicals optionally substituted by one or more OH groups; Z is a covalent bond or a linker spacer and A is a moiety capable of fixing a paramagnetic metal by chelation. Compounds of type (1) useful in the present invention are, for instance the polyalkylene-aminopolycarboxylic acids such as NTA, EDTA, DTPA, DOTA and like structures, possibly involving additional substituents; an example is the compound BOPTA which is a DTPA derivative carrying a benzyloxypropyl group.

13 Claims, 1 Drawing Sheet

US 6,241,968 B1

Figure 1:
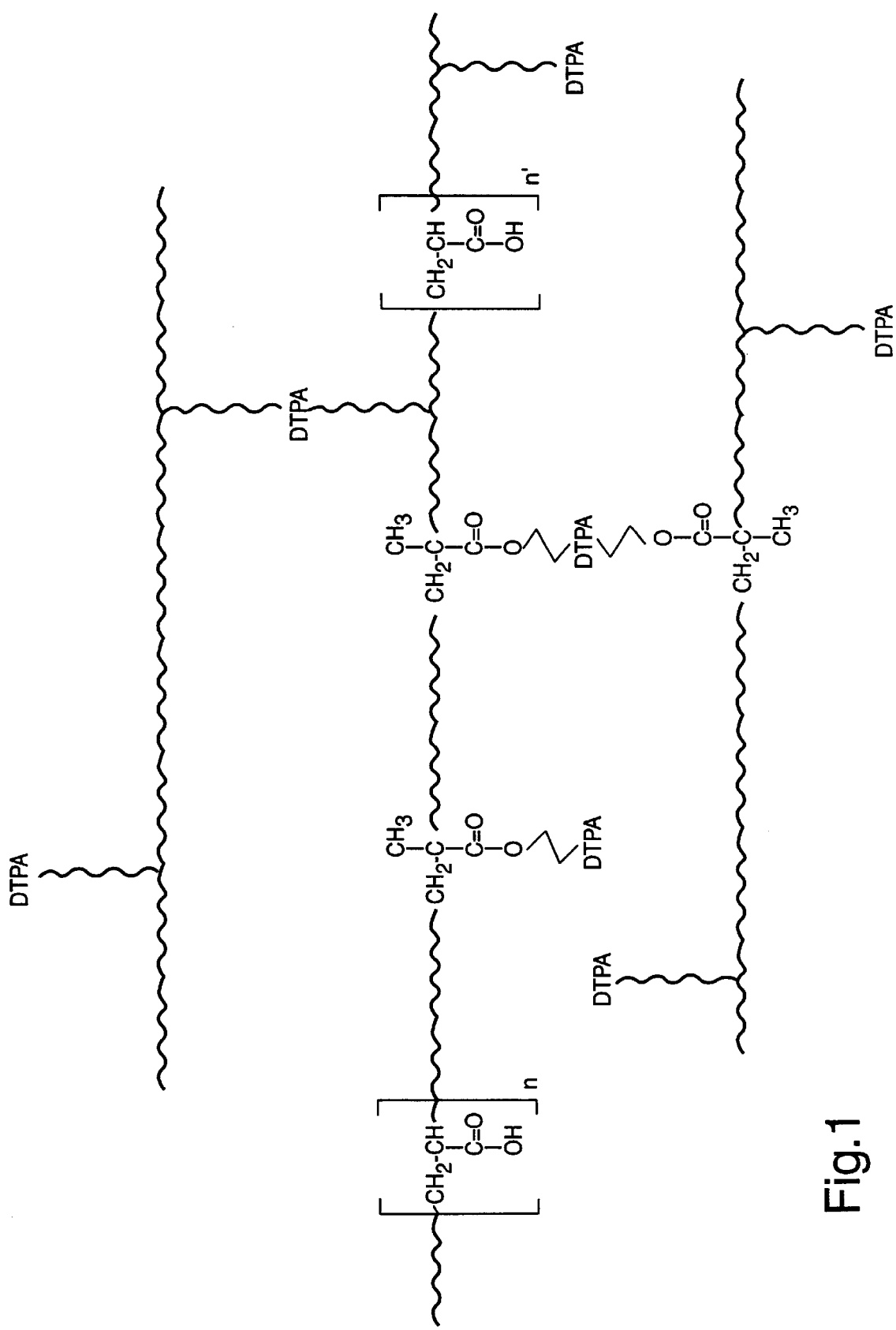

COMPOSITIONS FOR INCREASING THE MRI CONTRAST IN VISUALIZING THE DIGESTIVE TRACT OF PATIENTS

This is a division of application Ser. No. 08/997,453, filed Dec. 23, 1997, now U.S. Pat. No. 6,060,040, the entire content of which is hereby incorporated by reference in this application.

FIELD OF THE INVENTION

The present invention concerns innocuous ingestible or enterally administrable compounds and compositions which are used as contrast enhancer media or agents in nuclear magnetic resonance imaging (MRI) of the gasto-intestinal tract of animal and human patients. It also concerns methods for making the new contrast agents and their application in diagnostic imaging.

BACKGROUND ART

It is well known that MRI enables the direct electronic visualisation of internal organs in living beings and is therefore powerful help and guide in prognosis, medical treatment and surgery. This technique can often advantageously supplement or replace X-ray tomography as well as the use of radioactive tracer compounds which may have obvious undesirable side effects.

The whereabouts of MRI techniques applied to the imaging of body organs are summarised in EP-A-0 502 814 and need not be developed in detail here; suffice to say that the useful parameters pertaining thereto, i.e. the relaxation time factors $T_1$ and $T_2$ of the water protons in the direct environment of the organs under investigation are usually not sufficiently differentiated to provide sharp images when the measurements are carried out in the absence of contrast agents. The differences of the relaxation time constants between protons in various parts of the organs can however be enhanced in the presence, in the environment of the hydrated molecules under excitation, of a variety of magnetic species, e.g. paramagnetic (which mainly affect $T_1$) and ferromagnetic or superparamagnetic (which mainly affect the $T_2$ response). The paramagnetic substances include some metals in the ionic or organo-metallic state (e.g. $Fe^{+3}$, $Mn^{+2}$, $Gd^{+3}$ and the like, particularly in the form of chelates to decrease the intrinsic toxicity of the free metal ions). Ferromagnetic and superparamagnetic contrast substances preferably include magnetic particles of micronic or submicronic size, i.e. from a few microns down to a few nanometers, for instance particles of magnetite ($Fe_3O_4$), $\gamma\text{-}Fe_2O_3$, ferrites and other magnetic mineral compounds of transition elements.

Until now, MRI contrast agents designed for imaging the digestive tract have mostly included solid magnetic materials generally in particular form. This is so because to be effective, the contrast agents should more or less line the walls of the digestive tract, thus requiring bulk. Obviously paramagnetic species in water-soluble molecular form would not fit the foregoing requirements and, if used, they should be associated with bulk carriers.

For instance, EP-A-0 275 215 discloses MRI contrast enhancers for the investigation of the digestive tract comprising complexes of paramagnetic metal species like gadolinium, iron, manganese and the like associated with mineral particulate carriers such as alkaline-earth polyphosphates and apatite.

EP-A-0 083 760 discloses EDTA, DTPA and NTA chelates of paramagnetic metals chemically bonded to organic polymer carriers such as sepharose, dextran, dextrin, starch and the like.

Also in EP-A-0 299 920 there are disclosed complexes between paramagnetic metals such as Cr, Mn, Fe, Ni, Co, Gd, etc. and polysulfated oligosaccharides like sucrose or maltose, these complexes being used for MRI of the digestive tract.

U.S. Pat. No. 5,466,439 discloses diamidopolymers of conventional alkyleneaminopolycarboxylic chelatants such as EDTA, DTPA and the like, and their addition copolymers with methyl methacrylates. The structure of polyethylene diamide-DTPA obtained from ethylene diamine and DTPA dianhydride is given below for illustration:

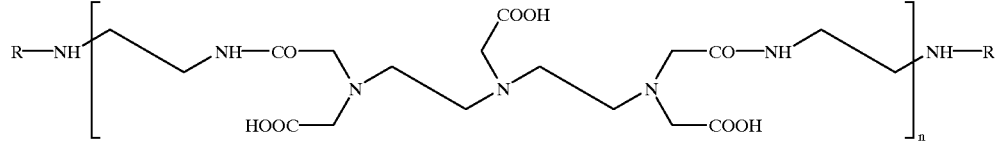

The polymeric chelatants are used to immobilize paramagnetic metals, e.g. Cr, Mn, Fe and the lanthanides, e.g. Gd, and the complexes administered orally for imaging the digestive tract.

Although the achievements of the prior art have merit, there is still need for more performant internal paramagnetic MRI contrast agents, more particularly in regard to bioadhesivity and controlled transit time in the digestive tract. The present invention is a forward step in the right direction.

DETAILED DESCRIPTION OF THE INVENTION

The invention provides, as contrast signal generators in MRI imaging of the digestive tract, paramagnetic metal chelates of novel acrylic compounds of formula $C(R^1R^2)$=$CR^3$—CO—Z—Z (1) and/or $C(R^1R^2)$=$CR^3$—CO—Z—Z—CO—$CR^3$=$C(R^1R^2)$ (2) in monomer, oligomer, homopolymer and copolymer forms, in which the $R^1$, $R^2$ and $R^3$ represent H or saturated or unsaturated $C_{1-10}$ aliphatic radicals optionally substituted by one or more OH groups; Z is a covalent bond or a linker spacer and A is moiety capable of fixing a paramagnetic metal by chelation.

Compounds of type 1 and/or 2 useful in the present invention are, for instance the polyalkylene-aminopropylcarboxylic acids such as NTA, EDTA, DTPA, DOTA and like structures, possibly involving additional substituents; an example is the compound BOPTA which is a DTPA derivative carrying a benzyloxypropyl group. Suitable mono and difunctional monomers involving DTPA are given below for illustration (formula III and III bis)

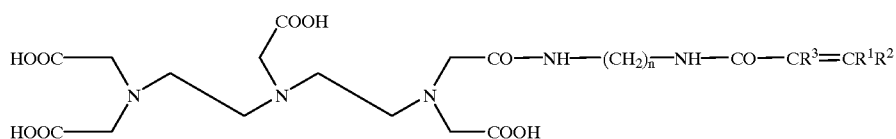

III

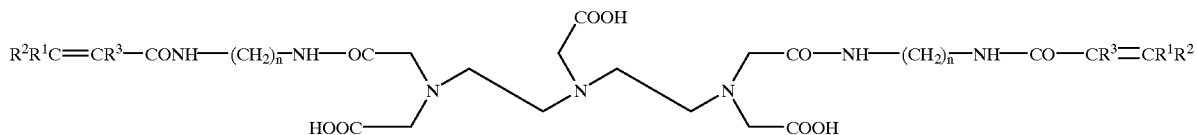

III bis

In these compounds, one or two of the carboxylic functions of DTPA has been derivatized to be connected to the acrylic moiety via an alkylene diamide bridge.

In other embodiments, other chelating moieties can be similarly associated to (1) and/or (2) such as those disclosed in K. Kumar et al., J. Liquid. Chromatography 17 (1994), 3735–3746 incorporated herein by reference. Preferred compounds are those in which Z is H (DO3A), carboxymethylene (DOTA), —CH$_2$—CHOH—CH$_3$ (HP-DO3A), or gadoteridol when in chelate form with Gd), —CH$_2$—CHOH—CHOH—CH$_2$OH (gadobutrol when in the form of chelate) and —CH(CH$_3$)COOH (DOTMA). Other suitable macrocyclic chelates are disclosed in documents WO87/05030 and WO89/01476 incorporated herein by reference.

Z being a bond or a lower aliphatic substituent (C$_{1-6}$) carrying one or more oxygen, nitrogen or sulfur containing functions (e.g. —OH, —SH, —NH$_2$, —O—, —S—, —NH—, —CO—, —COOH and the like).

In formula (1) or (2), the —CO— group is preferably linked by reaction to a hydroxy, amine or mercaptan function of Z via ester, amide or thioester bonds. For instance, Z can derive from a lower (C$_{1-6}$) alkylene diamine bridging unit, the N's of which are linked through amide bonds to the —CO—'s of (1) or (2). Formula II and II bis are examples of such connecting way

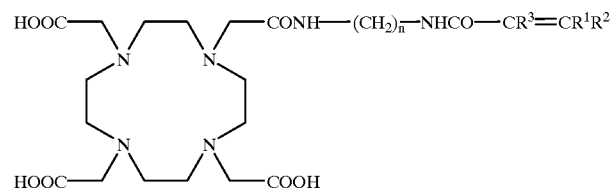

II

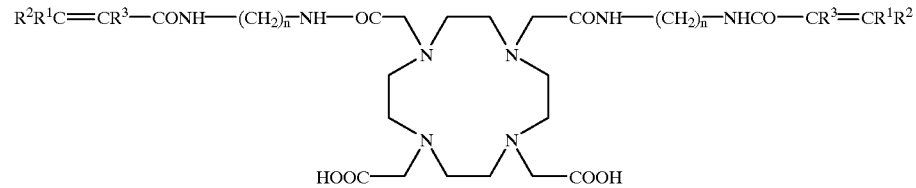

II bis

A can be for instance a molecule like that of formula I

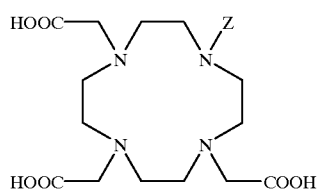

I in which n can be 2 to 6. Alternatively, Z can be derived from corresponding glycols or thioglycols.

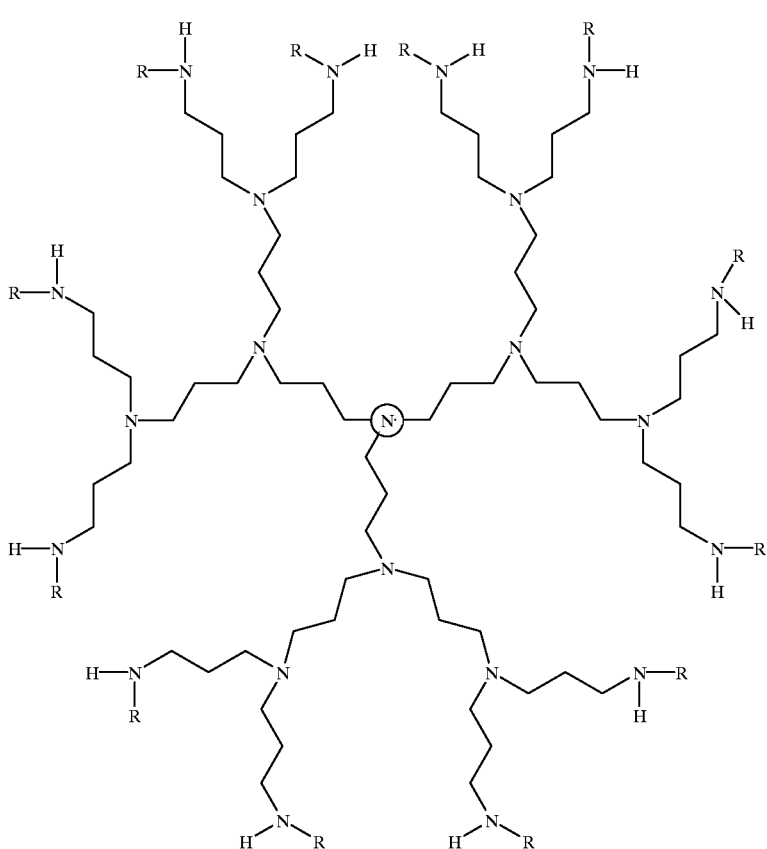

IV

In other embodiments, another class of macromolecular chelates useful in the present invention is that derived from "Starburst®" dendrimers exemplified by the structure (IV) above, in which at least one R is the acryloyl portion of formula (1), the other R's being derivatized chelatants of paramagnetic metals, e.g. isothiocyanato-DTPA (ITC-DTPA), SCN-Ph-NH-CO-CH$_2$-DO3A (IPA-DO3A), or having the formula

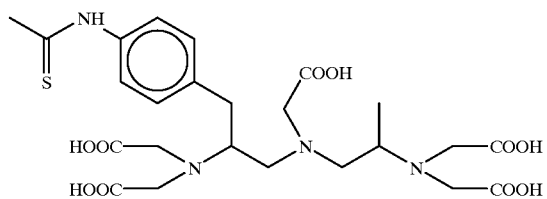

in ionic form. The foregoing dendrimer chelatants are disclosed in detail in the publication of E. C. Wiener et al., Magnetic Resonance in Medicine 31 (1994), 1–8, which is incorporated herein by reference.

The paramagnetic metals retained as complexes in the present polymer chelates include lanthanides, e.g. Gd and some transition elements including Fe, Mn, Cr and the like.

A general method to manufacture the chelatant compounds of the invention is based on the acylation with acryloyl derivatives of hydroxy, thiol, or amino derivatives of the chelating agents. The reaction is exemplified below using for illustration HP-DO3A and an acryloyl halide:

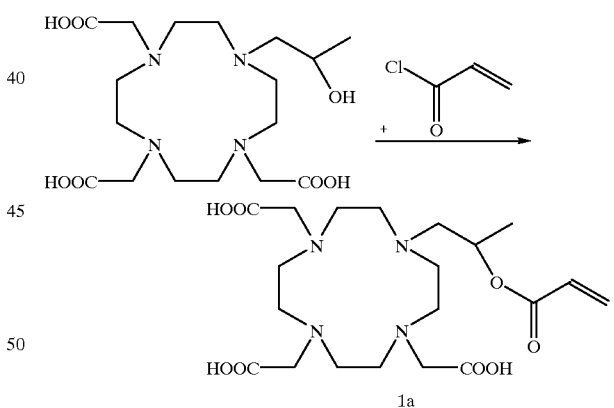

According to variant routes spacer-linkers are derived from alkylene bridges carrying terminal derivatizable functions like —OH, —SH and unsubstituted or monosubstituted amino groups. As an illustration, a bridging alkylene diamine (of which one terminal nitrogen is protected by a protective group [Pr], e.g. benzyl, tosyl, BOC or the like) is reacted with a chelatant N-polycarboxylic anhydride to provide a mixture of the corresponding monoamide and diamide; then, after deprotection of the free amino group, the mixture is acylated as in the foregoing scheme. The reactions are summarized below using for illustration EDTA and hexamethylene diamine

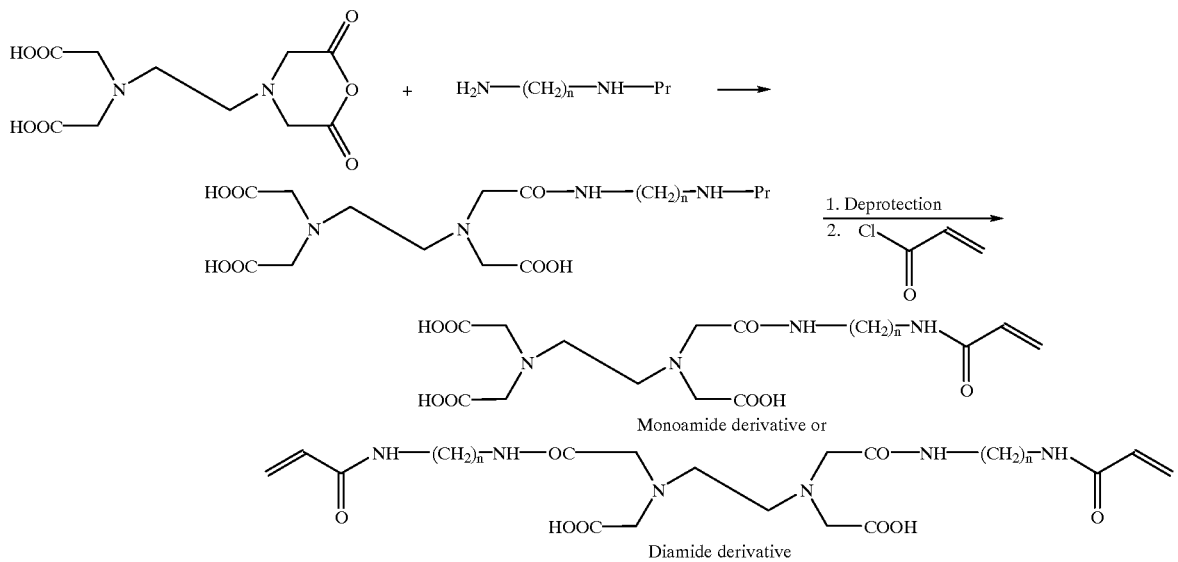

In another route a polyaminopolycarboxylic anhydride is reacted with a non-esterified —OH of a polyolacrylate. This may be illustrated using an EDTA anhydride and an excess of glycol monomethacylate as follows:

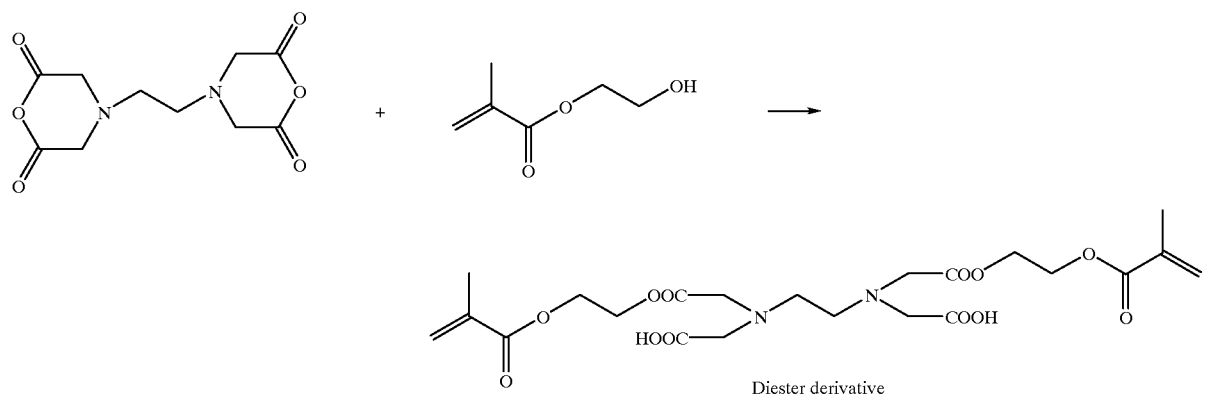

In addition, other preparation techniques are possible, for instance those mentioned in connection with the dendrimer chelatants mentioned heretofore.

The present monofunctional and/or difunctional monomers can be converted to various polymeric forms including homopolymers and copolymers with other olefinic monomers using conventional polymerization techniques, for instance radiations or chemical initiators like organic and mineral peroxides or peroxy-salts. As the bioadhesivity or acrylic polymers depends on the degree of cross-linking of the polymer, if this degree is low the bioadhesivity is poor; the polymer is water soluble and its usefulness as a contrast agent is compromised. On the other hand, if the degree of cross-linking is too high the polymer may be water swellable but its bioadhesivity is again poor and its usefulness for the intended purpose practically negligible. Hence, as a certain degree of cross-linking i.e. bioadhesivity is required, if a monofunctional monomer (1) is used, addition of a cross-linking agent (e.g. bis-acrylamide) is necessary. If, on the other hand, a bi-functional monomer of the invention (2) is employed the cross-linking is inherent and such monomer may require only addition of no or a very small amount of a cross-linking agent such as bis-acrylamide. Therefore, in the present invention, the use of the mixture of monomers (1) and (2) directly obtained by synthesis is preferred as schematically shown in FIG. 1. The extent of polymerization, i.e. the Mw of the polymerized products, can be controlled by adjusting as usual the polymerization conditions. In the present invention the degree of polymerization can vary in a wide range; from a few monomer units (oligomers) to several tens of units, the degree of polymerization being ruled by the properties sought of the end products. The paramagnetic metals can be complexed to the chelating moieties preferably at the polymer stage, but also at the monomer stage if necessary, this being then followed by polymerization.

The other olefinic monomers can include lower acrylates and methacrylates (esters of $C_{1-10}$ linear and cyclic unsubstituted or hydroxylated aliphatic alcohols), as well as acrylamide, acrylonitrile, maleic acid and the like. Polyfunctional olefinic compounds, for instance allyl ethers or acrylic esters of polyols (glycols, polyglycols sugars oligosaccharides, etc.) can also be useful as co-monomers to bring about some degree of crosslinking in the polymerization. The proportion of the other olefinic monomers relative to the monomers of the invention is advantageously 1–50% by weight but this can be overrun if desired.

In order to practically apply the polymer and copolymer compounds as contrast agents in the field of MR imaging, contrast composition are used comprising the compounds, either neat or with physiologically acceptable carrier phases and optionally other ingredients.

Thus, for an efficient and selective imaging of portions of the digestive tract, it is advantageous to select composition components and phases that have particular selective affinity for the gastric mucosa, e.g. phases which can form intestinal linings or coatings on all or selected portions of the internal lumen surfaces. Hence when the contrast compositions have special affinity for the gastric and intestinal mucosa, they will stay in immobilized layer form thereon or controllably transit through the digestive tract. The said carrier phase is preferably substantially water insoluble, although swellable by hydration and gel forming, and, when hydrated, has differential affinity for the gasto-intestinal mucosa, i.e. it adheres preferably to some areas thereof, thus forming luminal linings or coatings having specific magnetic contrast response patterns which enable improved visualization of specific portions of the oeso-gastro-duodenal tract. The polymer compounds of the invention already possess inherently such properties which can be enhanced and/or controlled by the further carriers or additives.

The present contrast compositions will therefore comprise the present chelate polymer or copolymer of acrylic acid optionally containing a proportion of other polymerizable monomers (generally di- or polyfunctional allyl ethers or acrylates) and optionally other bioadhesive polymers to impart a degree of water-insolubility and swelling capacity to form gels. Suitable polymers are available on the market under the names of Carbopol® or Polycarbophil®, for instance from the Goodrich Company. Other suitable polymers of comparable type are disclosed in EP-A-0 309 404 (included for reference) and comprise copolymers of acrylic acid with allyl ethers of glycols or sugars. Upon addition of water these polymers will form viscous dispersions of microgels which have strong affinity for internal mucous membranes. Furthermore, the gelling and swelling properties of such polymers are pH dependent; hence the volume, bulk and adhesive properties of the carrier can be controlled by adjusting the pH to a desired value at the administration stage. Other additional ingredients to the carriers may comprise materials having affinity for the membrane mucosa of the digestive tract and can include most luminal coating materials in use for treatment, protection of medication of gastro-intestinal regions, including for instance, adhesives containing bismuth oxide, aluminum oxide, montmorillonite and attapulgite designed for luminal applications. These materials also include cross-linked polymers such as polysiloxanes (Dimethicone®), magnesium and other metals alginates, bioadhesive pectins and carbohydrates polysubstituted with groups such as sulfate, phosphate, sulfonate and phosphonate. One convenient polysulfated carbohydrate is sucrose octasulfate (also named sucralfate). These may also include montmorillonite of the Beidel type which can assist as contrast agent in the MRI of the digestive tract of humans and animals, this being possibly due to some inherent magnetic properties of the montmorillonite.

The compositions of the invention may further comprise in admixture aqueous solutions of one or more water soluble polymers. These can be selected from water-soluble polymers which can form homogeneous solutions in aqueous media. The polymers which are convenient are for instance PEG, dextran, polyvinyl-pyrrolidone (PVP), and the like. The proportion of water soluble polymers to signal generating polymers therein preferably not exceeds 10% by weight of composition, more preferably 5%. Although the water-soluble polymers have no recognized specific affinity for the internal mucosa membrane of the digestive tract, they are useful for controlling the transit therethrough of the present bioadhesive paramagnetic polymers and more particularly when used in association with the optional further bioadhesive carrier phases.

Thus, since as already mentioned, the water-insoluble polymers (including the novel polymers and copolymers to function as signal generator in metal complex form) have the general property of getting hydrated with water and forming therewith substantially insoluble gels which more or less adhere to the membrane mucosa, the selection of further ingredients and the possible addition of water-soluble polymers, will provide compositions according to the invention having controllable transit time through the gastrointestinal tract and particular adhesion to selected portions thereof, thus enabling efficient NMR imaging of selected organs. Normally, the compositions using polymers having weak bioadhesion will permit faster transit than the compositions using polymers with strong bioadhesive character, hence controlled transit can be achieved with compositions in which weak-bioadhesive and strong-bioadhesive materials are admixed in suitable proportions. It has also been surprisingly found that the particular selection of polymers used in the compositions of the invention, i.e. polymers with enhanced affinity for mucosa membranes at low pH and/or soluble materials with high dispersive capacity provide generally excellent transverse and longitudinal luminal imaging homogeneity.

The present ingestible MRI contrast compositions are stable even at pH 1 and this is another advantage over products of the prior art using magnetite which may become toxic after attack by the digestive fluids. Bioadhesivity is particularly effective under acid or near neutral conditions. Hence control of bioadhesivity by pH control (optional presence of buffers) is another asset of the present invention.

The present polymers or copolymers complexed with paramagnetic metals can be administered neat or with additives as discussed above (contrast compositions) for lining the GI tract and aid, by functioning as contrast agents, in the MR visualizing of portions thereof. For manufacturing the contrast compositions according to the invention one usually admixes the signal generating polymers in complex form with the paramagnetic metals with other ingredients of a carrier phase. In one embodiment of a method for preparing contrast compositions according to the present invention, one admixes the present polymer (or copolymer) chelates by dry form with dry powder excipients or active ingredients. When used for internal MRI investigation, the composition can be used dry, in past form or rehydrated with water or a physiologically acceptable aqueous solution, this being for oral or enteral administration. In the case of oral administration, it can of course be flavored or perfumed using conventional flavor additives.

Thus for instance, in the case the carrier phase comprises a polymer of copolymer of acrylic acid, this can be prepared by copolymerizing a mixture of acrylic acid (and optionally other olefinic monomers) and one or more monomers according to the invention. The polymer is then treated with a solution of a paramagnet salt (e.g. $Gd^{3+}$, $Mn^{2+}$, $Fe^{3+}$, etc.) for immobilizing the metal ions in chelated form. Then, the metal loaded polymer is admixed with the optional other ingredients of the desired compositions. Optionally, the mixture can be dehydrated (for instance by freeze drying) and stored dry.

Then, for using the composition in the study of the digestive tract, the composition (when stored dry) is admixed with an aqueous phase (for instance saline) suitable for oral administration in order to provide a gel or paste which will adhere to a predetermined extent to the mucous membrane of the digestive tract and therefore will carry the contrast agent through said tract to the portion thereof to be visualized. As said hereinbefore, the rate of transfer and the transit time can be adapted by properly selecting the nature and degree of bioadhesion of the ingredients in the carrier phase. For this, variable proportions of contrast generating polymer, water-soluble carrier polymer and bioadhesive polymers are admixed together in the compositions, the proportions being selected to ensure a desired rate of transit. As an illustration, it was found that for NMR investigations, using a high proportion of dextran in rats gave a fast transit rate, while using mainly CMC gave non-accelerated transit. Using Carbopol® gave strongly retarded transit, particularly in the duodenum portion of the intestinal tract. The present contrast compositions may also advantageously comprise isoosmolarity agents which minimize loss or gain of water during intestinal transit, i.e. diffusion by osmosis; such agents may comprise carbohydrates such as sorbitol, mannitol, xylitol and the like.

During transit time, the patient under administration of a dose of the present compositions is subjected to periodical or continuous investigations using conventional MRI equipment, whereby the obtained processed images can thereafter be used for diagnostic or other medical applications.

The invention is now illustrated by the following practical examples.

EXAMPLE 1

Reaction of DTPA anhydride with 2-hydroxyethyl methacrylate (HEMA)

Fifteen mmol (5.36 g) of DTPA dianhydride (obtained by refluxing DTPA in acetic anhydride) were dissolved in 160 ml of dry DMF at 65° C. After cooling at room temperature, there was added thereto a solution of 0.44 g (3 mmol) of 4-pyrrolidinopyridine (catalyst), 15 mmol (1.92 ml) of β-hdyroxyethyl methacrylate (HEMA) and a trace of hydroquinone monomethyl ether (HQMEE—polymerization inhibitor) in 4 ml of dry DMF. After standing overnight at r.t., the solution was heated for 4 hrs at 65° C., then it was allowed to cool and 2.1 ml (15 mmol) of $NEt_3$ were added; the solution was again heated for a half Pa at 60° C. after which the solvents were removed under vacuum and the residue dispersed in 200 ml of ether under magnetic agitation. After filtration, the solid (7.73 g) was dissolved in 150 ml of water and the solution which had a pH of 2.5 was agitated for 1 hr with 25 g (55 mEq) of water-washed IRA120 resin (acidic form). The filtrate was rotoevaporated and dried overnight under vacuum. The residue was taken with 50 ml of $CH_2$—$Cl_2$ at 50° C., filtered and the filtrate precipitated with 200 ml of ether; yield 5.88 g of powder (HEMA-DTPA) corresponding to a mixture of mono and diacrylic derivatives of DTPA with the respective formulae

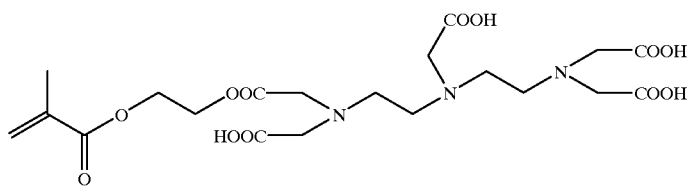

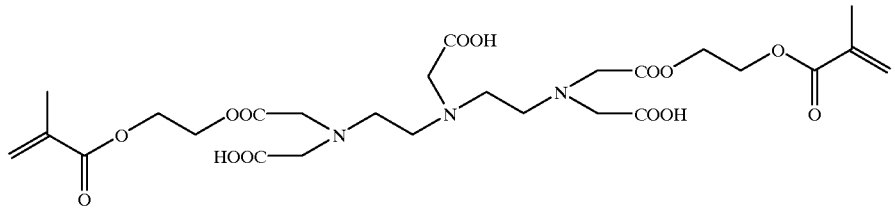

EXAMPLE 2

(A) The reaction of DTPA dianhydride and t.butoxycarbonyl-hexamethylene diamine

Fifteen mmol (5.36 g) of DTPA dianhydride were dissolved in 160 ml of dry DMF at 65° C. After cooling at room temperature, there were added thereto a DMF (25 ml) solution (prepared at 40° C.) of 15 mmol (3,79 g) of t.butoxycarbonyl-hexamethylene diamine hydrochloride (BOC-1,6-diamino-hexane.HCl) and 2.1 ml (15 mmol) of triethyl-amine. The mixture was heated to 65° C. for 1 hr, after which was allowed to cool, 5.5 ml of $H_2O$ were added, and it was left to stand overnight at room temperature. The solvents were removed under vacuum and the residue dissolved in 200 ml of water to give a solution of pH of which was brought to 9 with NaOH solution. After filtration, 1N HCl was added to make the pH, 1.2; this resulted into a precipitate which was collected (yield 5.36 g) corresponding to a mixture of the monoamide and diamide of DTPA of formulae

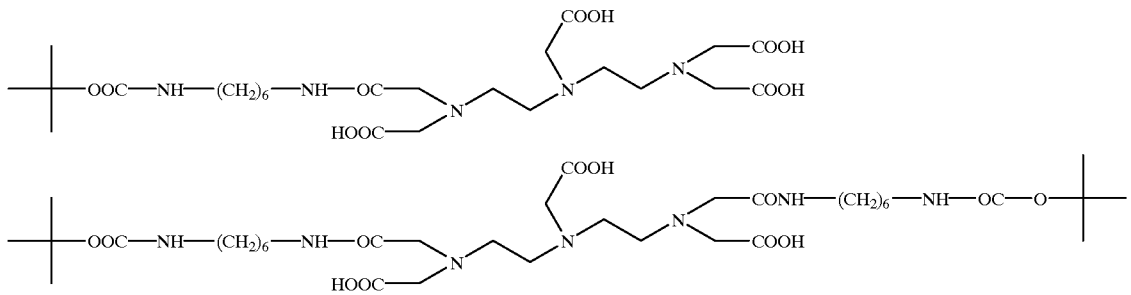

The t.BOC protection was removed by 1 hr agitation with 25 ml TFA (trifluoracetic acid) in 50 ml methylene chloride, after which was solvents were eliminated under vacuum and the remaining solid purified by crystallization. The product mixture was soluble in water, MeOH, EtOH and acetone; it was insoluble in ether, hexane, THF and dioxane.

(B) Reaction of the mono- and di-amido-DTPA with acryloyl chloride

The above mixture of products was dissolved in about 100 ml of water and the pH was raised to 8 with NaOH. At 2° C. (ice bath), there were added progressively by portions 2.3 ml of acryloyl chloride; after each 0.5 ml portion, the pH was readjusted to 8 with conc. NaOH. After the end of the addition, the mixture was allowed to come to room temperature, the pH being controlled with NaOH to stabilize at 7.5. A trace of HQMME was added and the solution was filtered.

The solution was acidified to pH 1 with HCl and evaporated. The residue was taken with 150 ml of MeOH, filtered, concentrated to 75 ml on the rotavapor and 400 ml of ether added which caused the separation of an oil. This oil was triturated with ether whereby crystals of the desired compound (AHMDA DTPA) corresponding to a mixture of the mono- and di-acrylic derivatives of DTPA with the respective formulae diamine (TEMED), neutralizing to pH 7.5 with HCl and making to 100 ml final volume with water.

AA (acrylic monomer) solution:

There was also prepared a 1M, pH 7.5, solution of Na acrylate (AA) by dissolving 6.93 ml of acrylic acid in 50 ml of ice-water, neutralizing with NaOH and making it to 100 ml with distilled water.

1.09 g of AHMDA-DTPA (see Example 2) were dissolved in 3 ml of water and neutralized to pH 7.5 with 1N NaOH (final volume 5 ml). To this were added 8 ml of the AA solution and 3 ml of the Tris-TEMED solution. The mixture was filtered on a 0.2 μm membrane, then under bubbling of $N_2$, there was added 0.3 ml of a 5% (W/V) potassium persulfate solution and the vessel was tightly stoppered. The solution became viscous and a gel developed. This product was used to chelate Gd by adding 2.5 mmol (0.93 g) of $GdCl_3.6H_2O$.

(B) Complexation of Gd with AHMDA-DTPAA and copolymerization with acrylic acid

A solution of AHMDA-DTPA was prepared from 1.09 in 2 of water, neutralized to pH 7.5 with alkali. To this were added dropwise a solution of 0.93 g (2.5 mmol) of $GdCl_3.6H_2O$ in 0.5 ml of water, the pH of the mixture being adjusted to 7 with alkali after each drop. A precipitate formed which dissolved partly after diluting with 3 ml of

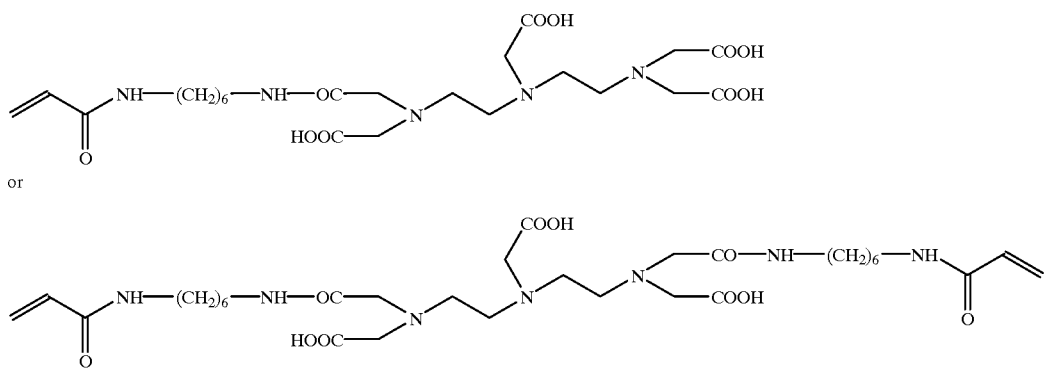

The crude product was recrystallized from alcohol or water/acetone.

EXAMPLE 3

(A) Copolymerization of AHMDA-DTPA with acrylic acid and complexation of Gd

Tris-TEMED solution:

A buffer solution (0.2M Tris-0.2M TEMED) was prepared using 2.42 g tris-(hydroxymethyl)-aminomethane in about 60 ml of water, adding 3.03 ml of tetramethylethylene Tris-TEMED solution. The solution was added to 8 ml of AA solution plus 70 mg of bis-acrylamide cross-linker whereby a precipitate formed which was eliminated by centrifugation and filtration of the supernatant. The solution was placed in a polymerization tube and saturated with $N_2$, after which 0.3 ml of 5% persulfate were added and the tube was stoppered. A gel formed overnight which was ground and calibrated through a 1 mm grating, and the resulting particles repeatedly washed (first by decantation and thereafter by draining on a Buchner funnel) with PBS and water to give a final volume of 420 ml; the gel was dried, yield 0.7 g of dry product.

EXAMPLE 4

Complexation of Gd with HEMA-DTPA and copolymerization with acrylic acid

The product from Example 1 (HEMA-DTPA) (505 mg) was dissolved in 1 ml of water and neutralized to pH 7.5 with alkali. To this were added dropwise a solution of 0.47 g (1.25 mmol) of $GdCl_3.6H_2O$ in 0.5 ml of water, the pH of the mixture being readjusted to 7 with alkali after each drop. Then, there were added 1 ml of the Tris-TEMED solution, 50 mg of bis-acrylamide and 4 ml of the AA solution (see the previous Example). The solution was filtered on a 0.2 µm filter and placed in a polymerization tube and bubbled with $N_2$. Five % persulfate solution (0.3 ml) was added and the tube was closed with a stopper. A white gel formed overnight which was calibrated on a 1 mm mesh screen, the particles being thereafter thoroughly washed with water. The total volume of the gelled particles was 150 ml for 0.29 g dry weight. A schematic formula of the product of the invention is shown in FIG. 1.

EXAMPLE 5

Relaxation experiments using the following copolymers:

A)=HEMA-DEPA/AA.

B)=AHMDA-DTPA/AA.

Two samples of gels A and B were prepared according to the disclosures of the previous Examples but without the Gd salt. The ingredients were as follows:

A) 505 mg HEMA-DTPA in 2 ml of water, pH 7.5;
   2 ml of Tris-TEMED solution;
   50 mg of bis-acrylamide cross-linker;
   4 ml of 1M AA solution (see example 3).

B) 1.09 g AHMDA-DTPA in 3 ml of water, pH 7.5;
   Tris-TEMED 3 ml; bis-acrylamide 70 mg; AA 8 ml.

Both solutions were filtered and polymerized under $N_2$, then the gels were calibrated and washed as in the previous Examples. The yields were: A) 250 ml of wet gel (8.22 mg of dry gel/5 ml of wet gel)=44%. B) 200 ml of wet gel (18.26 mg of dry gel/5 ml of wet get)=38%.

Suspensions (pH 8.5) were made from, respectively 50 ml of gel A) and 20 ml of gel B). Each suspension was treated as disclosed in the previous Examples with a solution of $GdCl_3.6H_2O$ (186 mg/1 ml $H_2O$), the pH being maintained at about 7.5 with added alkali. The gels which had become whitish were drained on a Buchner funnel, and washed with water and PBS; then the particles were resuspended in water to provide gel suspensions A and B which contained:

A) 33.43 mg of dry polymer/5 ml of gel;

B) 60.76 mg of dry polymer/5 ml of gel.

Proton spin relaxivities of the foregoing gel suspensions (with and without the gadolinium) were measured using a Minispec PC-120 (Bruker) apparatus, operating under 0.47 Tesla (20 MHz). EDM 510A (EDM=Experiment Definition Module) was used to measure the spin-lattice relaxation time $T_1$ by the "inversion recovery" method. EDM 610A was used to measure the spin-spin relaxation time $T_2$ by the Carr-Purcell-Meiboom-Gill (CPMG) technique. The results gathered in the next Table are also expressed as $1/T_1$ and $1/T_2$ in time reciprocal units $s^{-1}$.

TABLE I

| Sample | $T_1$ (sec) | $1/T_1$ | $T_2$ (sec) | $1/T_2$ |
| --- | --- | --- | --- | --- |
| A) without Gd | 1.977 | 0.51 | 2.9498 | 0.34 |
| A) with Gd | 0.0974 | 10.26 | 0.04902 | 20.4 |
| B) without Gd | 2.277 | 0.44 | 1.858 | 0.54 |
| B) with Gd | 0.1063 | 9.41 | 0.9696 | 10.31 |

The results from the above Table show that the presence of Gd strongly increases the $1/T_1$ and $1/T_2$ values.

EXAMPLE 6

Copolymerization of HEMA-DTPA or ADMDA-DTPA with acrylamide and thereafter relaxation experiments using the following copolymers:

C)=HEMA-DTPA/Acrylamide

D)=AHMDA-DTPA/Acrylamide

Samples of gels, C and D, containing respectively copolymerized HEMA-DTPA/acrylamide and AHMDA-DTPA/Acrylamide were prepared according to the directions in Examples 3–5 using the following ingredients:

C) 505 mg of HEMA-DTPA,
   2.5 ml of Tris-TEMED solution, pH 7.5,
   4 ml of 1M acrylamide solution (284 mg),
   35 mg of bis-acrylamide cross-linker D) 1.09 g of AHMDA-DTPA,
   5 ml of Tris-TEMED solution, pH 7.5,
   8 ml of 1M acrylamide solution (569 mg),
   70 mg of bis-acrylamide cross-linker After filtration, the solutions were polymerized with persulfate under $N_2$, then the resulting gels were ground, calibrated and washed as in the previous Examples. The yields were:

C) 65 ml of wet gel (53.95 mg of dry gel/5 ml)=77%;

D) 100 ml of wet gel (32.03 mg of dry gel/5 ml)=35%

Gel C (23 ml) and gel D (40 ml), respectively, were treated with 0.8 ml of a 0.5M solution of $GdCl_3.6H_2O$ as in the previous Examples, the pH being maintained around 7.5 by the addition of alkali. The gels were drained on a Buchner funnel, and washed with water and PBS; then the particles were resuspended in water to provide gel suspensions A and B which contained:

C) 32.13 mg of dry polymer/5 ml of gel;

D) 41.96 mg of dry polymer/5 ml of gel.

Proton spin relaxivities of the foregoing gel suspensions (with and without the gadolinium) were measured as in the previous Example. The results gathered in Table II are also expressed in the same manner as in Table I.

TABLE II

| Sample | $T_1$ (sec) | $1/T_1$ | $T_2$ (sec) | $1/T_2$ |
| --- | --- | --- | --- | --- |
| C) without Gd | 2.031 | 0.49 | 3.1042 | 0.32 |
| C) with Gd | 0.0547 | 18.3 | 0.0537 | 18.6 |
| D) without Gd | 2.430 | 0.41 | 1.925 | 0.52 |
| D) with Gd | 0.0103 | 97.1 | 0.0347 | 28.8 |

Comparing the results of Table II above with that of Table I show that the Gd complexes of the acrylamide copolymers provide better relaxation than the corresponding acrylic acid copolymers.

EXAMPLE 7

Copolymer Preparation 505 mg of HEMA-DTPA prepared according to Example 1 was dissolved in 2.5 ml of water and the pH was adjusted to 7.5 with NaOH solution. Then there was added 3 ml of Tris-TEMED solution and thereafter a solution of 372 mg (1 mmol) of $GdCl_3 \cdot 6H_2O$ in 0.5 ml $H_2O$. The pH was readjusted to 7.5 as above, then 4 ml of 1M acrylamide (4 mmol, 284 mg) to provide a final volume of 14 ml. After filtering over a 0.2 μm filter into a polymerization tube, there was added therein under $N_2$ bubbling 0.1 ml of 5% $K_2S_2O_8$ solution and the tube was stoppered. The polymer which formed overnight was precipitated with 200 ml EtOH, separated by decantation, washed with EtOH and the solid-separated by centrifugation. The solid was redissolved in 15 ml $H_2O$ and dialyzed against 3 successive 1 liter water portions to completely remove uncomplexed Gd. The liquid was finally freeze-dried to provide 0.4 g (42%) of polymer. The gadolinium proportion in the polymer was measured by atomic absorption spectrography and was found to be 49 mg/g of polymer.

Relaxation measurements were carried out using a solution of 100.5 mg of complexed polymer in 20 ml of $H_2O$ which corresponds to a 1.553 mM Gd solution. The following relaxivity values ($r_1$ and $r_2$) expressed in $(mM \cdot s)^{-1} = 1/T$ for a 1 mM Gd concentration were obtained:

| Sample | $T_1$ (ms) | $r_1 (mM \cdot s)^{-1}$ | $T_2$ (ms) | $r_2 (mM \cdot s)^{-1}$ |
|---|---|---|---|---|
| HEMA-DTPA/ acrylamide copolymer | 55.1 | 11.7 | 54.9 | 11.7 |

This indicates that the relaxivities of the foregoing complex are twice that of Gd-DTPA.

If in the foregoing Examples, there was used instead of the acryloyl derivatives of DTPA the esters of acrylic or methacrylic acid with N-hydroxyalkylated tetraazacyclododecane chelatants such as

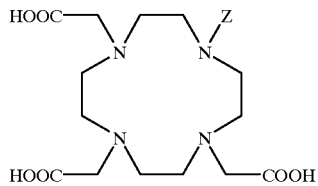

I in which $Z = -CH_2-CH_2OH$, $-CH_2-CHOH-CH_3$, $-CH_2-CHOH-CH_2OH$ and $-CH_2-CH_2-CHOH-CH_2OH$ as well as the compounds

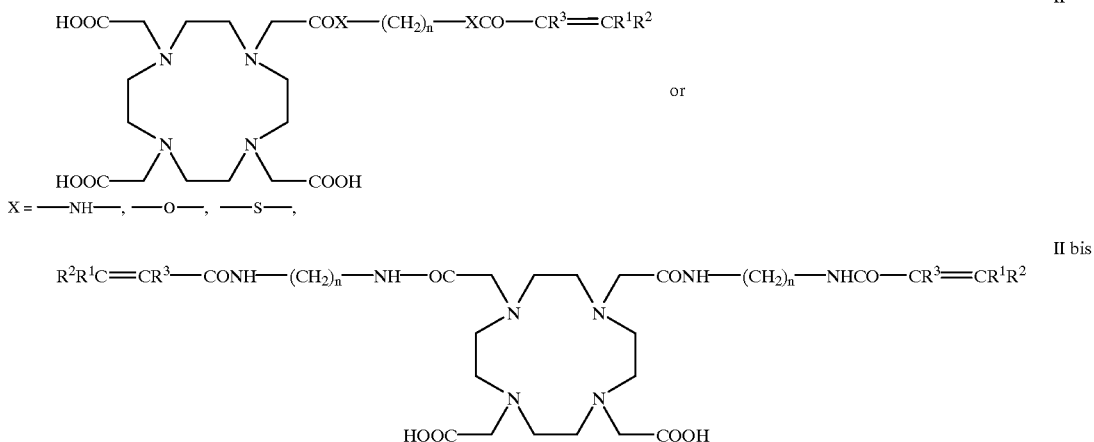

in which n can be 2 to 6, comparable results were observed.

EXAMPLE 8

Imaging Experiments

Five ml of polymer solutions according to Example 7 were administered orally by intubation to Male Sprague Dawley rates after 24 hours of fasting. The animals were anesthetized 10 min later with Pentotal (30 ml/kg). Transversal MR images were then taken on an Esaote ESATOM 5000 imager equipped with a special 8 cm i.d. RF receiver coil, using a slice of 2 mm, a F.O.V. of 15.9×15.9 cm, and a matrix size of 128×256. $T_2$ weighted images (SE 200/70/1), were acquired as well as $T_1$ weighted images (SE 500/16/2), and intermediate scan images (SE 350/50/2). For the $T_2$ weighted and intermediate scan images gradient moment nulling techniques were used in order to minimize respiratory artifacts. The $T_2$ weighted and intermediate scan images show a clear delineation of the darkened and expanded bowel loops. Especially the 350/50/2 image showed very clearly the single loops of the small intestine. The wall of the loops could be clearly observed. A cross section of the colon and of a kidney were also seen as well as abdominal and dorsal muscles. The contrast media was distributed evenly over the whole GI tract.

What is claimed is:

1. An MRI contrast enhancer compound consisting of a complex of MRI-responsive paramagnetic metals chelated with an acrylic cycle chelate compound of the formula:

$$(R^1R^2)C=CR^3-CO-Z-A \qquad (1)$$

in monomer, oligomer, homopolymer or copolymer form, in which $R^1$, $R^2$ and $R^3$ represent H or a saturated or an unsaturated $C_{1-10}$ aliphatic radical optionally substituted by one or more OH groups; Z is a covalent bond or a spacer linker and A is a cycle chelate moiety capable of complexing a paramagnetic metal by chelation.

2. The MRI contrast enhancer compound of claim 1 in which A has formula I

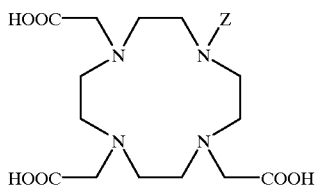

I in which Z is a bond to connect A to the —CO— of (1), or a lower aliphatic $C_{1-6}$ bridging substituent carrying one or more oxygen, nitrogen or sulfur containing functions selected from —OH, —SH, —$NH_2$—, —O—, —S—, —NH—, —CO— and —COOH, the —CO— function in formula (1) being linked to Z via an ester, thioester or amido bond.

3. The MRI contrast enhancer compound of claim 1 in which the cycle chelate moiety is linked to the acrylyl portion of (1) through an alkylene diester, xanthogenate or diamide bridging unit involving a carboxylic function of the cycle chelate chelatant.

4. The MRI contrast enhancer compound according to claim 3 of formula II

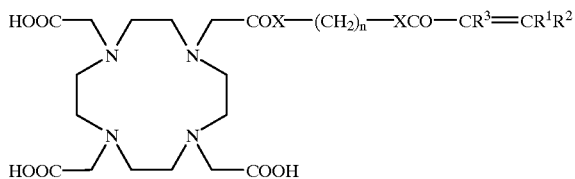

II in which X is —NH—, —O— or —S— and n is 2–6.

5. The compound of claim 2 in which Z is a direct bond, acetoxy, $CH_2$—$CH(CH_3)$—O—, —$CH_2$—CHOH—CHOH—$CH_2$O—, or —$CH(CH_3)COO$—.

6. An MRI contrast composition for MR imaging the digestive tract of humans and animals comprising together with a carrier or diluent paramagnetic metals chelated with a compound of claim 1 in homo- or copolymer form.

7. The composition of claim 6 in which the copolymer includes an olefinic monomer selected from lower acrylate and methacrylate esters of $C_{1-10}$ linear and cyclic unsubstituted or hydroxylated aliphatic alcohols, acrylamide, acrylonitrile, maleic acid and polyfunctional olefinic compounds.

8. The MR imaging compound of claim 6 in the form of pellets.

9. A method of MR imaging a patient's gastrointestinal tract or a portion thereof comprising:

(a) administering to the patient to be imaged an imaging amount of a compound of an acrylic cycle chelate compound of the formula

 (1) and/or

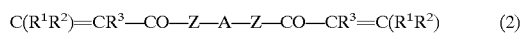 (2)

in monomer, oligomer, homopolymer or copolymer form, in which $R^1$, $R^2$ and $R^3$ represent H or a saturated or unsaturated $C_{1-10}$ aliphatic radical optionally substituted by one or more OH groups; Z is a covalent bond or a spacer linker and A is a chelatant moiety capable of complexing a paramagnetic metal by chelation, and thereafter (b) MR imaging the patient.

10. The method of claim 9 in which the cycle chelate moiety is linked to the acrylic portion of (1) or (2) through an alkylene diester, xanthogenate or diamide bridging unit involving one or two carboxylic functions of the cycle chelate.

11. The method of claim 9 in which A has formula I

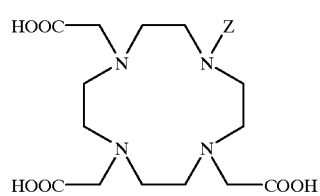

I in which Z is a bond to connect A to the —CO— of (1), or a lower aliphatic $C_{1-6}$ bridging substituent carrying one or more oxygen, nitrogen or sulfur containing functions selected from —OH, —SH, —$NH_2$, —O—, —S—, —NH—, —CO— and —COOH, the —CO— function in formula (1) being linked to Z via an ester, thioester or amido bond.

12. The method of claim 10 of formula II

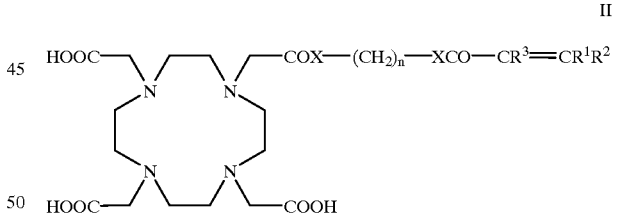

II in which X is —NH—, —O— or —S— and n is 2–6.

13. The method of claim 9 in which Z is a direct bond, acetoxy, $CH_2$—$CH(CH_3)$—O—, —$CH_2$—CHOH—CHOH—$CH_2$O—, or —$CH(CH_3)COO$—.

* * * * *